United States Patent [19]
Freeman

[11] Patent Number: 4,808,154
[45] Date of Patent: Feb. 28, 1989

[54] PHACOEMULSIFICATION/IRRIGATION AND ASPIRATION SLEEVE APPARATUS

[76] Inventor: Jerre M. Freeman, 1509 Peabody, Memphis, Tenn. 38104

[21] Appl. No.: 545,494

[22] Filed: Oct. 26, 1983

[51] Int. Cl.⁴ .............................................. A61B 17/20
[52] U.S. Cl. ....................................... 604/22; 128/305
[58] Field of Search .................. 433/118, 119; 604/22; 128/305, 244; 138/111, 113, 115, 116, 44

[56] References Cited

U.S. PATENT DOCUMENTS

| | | | |
|---|---|---|---|
| 2,432,641 | 12/1947 | Wilson | 222/568 |
| 3,589,363 | 6/1971 | Banko | 604/22 |
| 3,945,375 | 3/1976 | Banko | 604/22 |
| 3,948,273 | 4/1976 | Sanders | 604/280 |
| 4,223,676 | 9/1980 | Wuchinich et al. | 604/22 |
| 4,370,131 | 1/1983 | Banko | 433/119 |
| 4,516,398 | 5/1985 | Wuchinich | 604/22 |

Primary Examiner—C. Fred Rosenbaum
Assistant Examiner—J. L. Kruter
Attorney, Agent, or Firm—Bradford E. Kile

[57] ABSTRACT

A tip or probe extends through a hollow cylindrical base and coaxially projects through a cylindrical sleeve member connected to the base. The cylindrical sleeve member is provided with at least one internal, longitudinally extending, rib member to guide a flushing fluid through the cylindrical member and to isolate interior wall portions of the cylindrical sleeve from the tip member.

5 Claims, 2 Drawing Sheets

PHACOEMULSIFICATION/IRRIGATION AND ASPIRATION SLEEVE APPARATUS

BACKGROUND OF THE INVENTION

The present invention relates to a phacoemulsification/irrigation and aspiration sleeve apparatus which is useful during the removal of a cataract lens from a human eye.

The concept of implanting an intraocular lens, as a replacement for an opaque or cloudy cataract lens of a human eye, was suggested as early as 1766 by Casanova in his memoirs. It has been only within the last 30 years or so, however, that theory and desire have become a practical reality. In this connection, the first lens implantation is believed to have been carried out in 1949 by Dr. Harold Ridley at the St. Thomas Hospital in London. A lens was inserted into the posterior chamber of the eye of a woman of about 60 years of age following cataract extraction. Dr. Ridley's early efforts achieved a degree of success and ophthalmic surgeons began implanting lens composed of polymethylmethacrylate (PMMA) within the posterior chamber of human eyes following extracapsular removal of cataracts to restore binocular vision to patients.

Although certain drawbacks and complications accompanied successes, the art has continually progressed over the years and in 1982 it has been estimated that 500,000 cataract extractions were performed in the United States alone.

A cataract lens extraction process may be performed by a variety of techniques, however, one extracapsular extraction technique comprises making a 100 to 140 degree incision around the corneal rim of the eye and the lens is removed as a unit by manipulation of a lens loop instrument through a dilated or undilated iris. Although this extracapsular technique has been widely utilized, there has been increased attention in recent years toward another form of extracapsular cataract surgery. In this type of operative procedure, the capsule surrounding the cataract, or cloudy crystalline lens, is opened (usually anteriorly) and the cataract material is evacuated leaving the remainder of the capsular bag intact along with the zonules. This leaves the compartmentalization of the eye essentially intact and contributes to the stability of the eye. Many surgeons believe that this stability results in a lower complication rate which is particularly significant with an increasing frequency of artificial lens-implantation.

In the above connection, an extracapsular technique known as phacoemulsifacation and aspiration has been developed by a Dr. Kelman and his associates wherein an ultrasonic vibrating tip is inserted through a small corneal incision of three millimeters or so. The ultrasonic tip operably emulsifies the cataract, in situ. A co-axial sleeve extends along the ultrasonic tip and permits a simultaneous infection of a saline flushing solution to suspend particles of lens material and to simultaneously cool the vibrating tip member. The ultrasonic tip is fashioned with an axial bore and a vacuum is drawn on the bore to aspire the emulsified lens material and fluid co-axially through the ultrasonic tip.

Although the Kelman unit has been refined and improved over the years, certain disadvantages persist. In this connection, in order for the ultrasonic probe to exhibit a desired vibratory motion, relatively free from damping, the surrounding sleeve is composed of a soft pliable elastomeric material. It has been found that in some instances of operative procedures, and angles of utilization, the soft sleeve collapses or deflects against the ultrasonic probe. When the sleeve is pushed against the rapidly vibrating probe, the probe and sleeve tend to overheat due to friction and damage the delicate corneal or sclera tissue of the eye. In addition prior sleeves have tended to permit a random non-uniform flow pattern of fluid around the ultrasonic tip such that zones of elevated temperature may develop on the tip.

In addition to phacoemulsification and aspiration, certain instances occur when irrigation and aspiration are desired without concomitant phacoemulsification. In such systems, the central probe does not vibrate, however, it is still important to be able to insure a generally uniform irrigation throughout the range of angular probe manipulation. In the past, relatively pliable sleeves have tended to collapse and block a steady flow of irrigation fluid when a handpiece is manipulated to the right or left.

The difficulties suggested in the proceeding are not intended to be exhaustive, but rather are among many which may tend to reduce the effectiveness and satisfaction with prior phacoemulsification and aspiration devices. Other noteworthy problems may also exist. Those presented above, however, should be sufficient to demonstrate that phacoemulsification and aspiration devices appearing in the past will admit to worthwhile improvement.

OBJECTS OF THE INVENTION

It is therefore a general object of the invention to provide a novel phacoemulsification/irrigation and aspiration sleeve apparatus which will obviate or minimize difficulties of the type previously described.

It is a specific object of the invention to provide a phacoemulsification/irrigation and aspiration sleeve apparatus wherein the flow of saline flushing and cooling fluid around an ultrasonic probe is facilitated.

It is a related object of the invention to provide a novel phacoemulsification/irrigation and aspiration sleeve apparatus wherein the flow of cooling fluid is evenly distributed annularly around an ultrasonic probe to facilitate cooling and lubrication with respect to the sleeve.

It is another of the invention to provide a novel phacoemulsification/irrigation and aspiration sleeve apparatus wherein fluid flow around an ultrasonic probe is controlled and advantageously directed in a desirable cooling mode.

It is a further object of the invention to provide a novel phacoemulsification/irrigation and aspiration sleeve apparatus wherein contact of the sleeve with an ultrasonic probe is minimized even during highly angled phacoemulsification procedures.

It is still another object of the invention to provide a sleeve for use with phacoemulsification and aspiration as well as irrigation and aspiration which will resist collapse of the sleeve upon a central aspirating probe.

It is yet another object of the invention to provide a novel phacoemulsification/irrigation and aspiration sleeve apparatus wherein enhanced cooling of an ultrasonic tip is achieved without damping ultrasonic vibration of the operating tip.

BRIEF SUMMARY OF A PREFERRED EMBODIMENT OF THE INVENTION

A preferred embodiment of the invention which is intended to accomplish at least some of the foregoing objects comprises a phacoemulsification/irrigation and aspiration sleeve apparatus having a hollow cylindrical based member operable to be connected to a handpiece of a phacoemulsification/irrigation and aspiration unit. A tip or probe extends through the hollow cylindrical base and coaxially projects through a cylindrical sleeve member connected to the base. The cylindrical sleeve member has an internal diameter greater than the external diameter of the tip or probe thereby forming an annular passage around the tip member to conduct a lens flushing fluid around the probe and into a zone of lens aspiration at the distal end of the tip member. The cylindrical sleeve is provided with at least one internal, longitudinally extending, rib member to guide the flushing fluid through the cylindrical member and to isolate interior wall portions of the cylindrical sleeve from the tip member.

THE DRAWINGS

Other objects and advantages of the present invention will become apparent from the following detailed description of preferred embodiments thereof taken in conjunction with the accompanying drawings; wherein.

DETAILED DESCRIPTION

Context of the Invention

Figure 1:
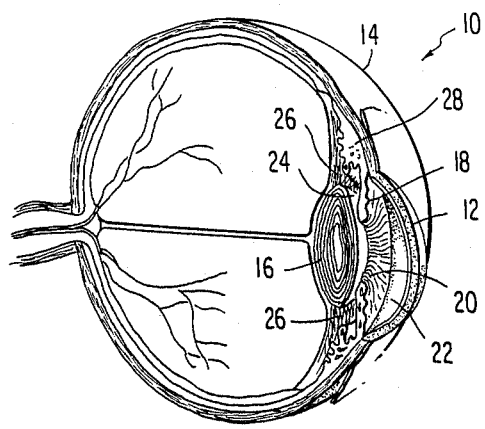
FIG. 1 is an axonometric cross-sectional view of a human eye disclosing a natural lens positioned within a posterior chamber of the eye.

Before providing a detailed description of preferred embodiments of the subject invention, it may be worthwhile to briefly outline the context of the instant invention. In this connection, FIG. 1 discloses an axonometric cross-sectional view of a human eye 10. The posterior half of the eyeball closely approaches a spherical shape, while a forward or anterior portion is provided with a roughly spherical segment of sharper curvature which is transparent and is called the cornea 12. An opaque posterior portion of the eye is known as the sclera 14.

The cornea 12 is constructed in such a way as to serve as a refracting medium in addition to forming the exterior wall of the eyeball. The cornea is a strongly convergent lens and possesses approximately 2½ times the focusing power of an internal natural crystaline lens 16. An iris 18 of variable aperture, known as a pupillary opening or pupil 20, is located between the cornea 12 and the crystaline lens 16 and divides the eye into an anterior chamber 22 in front of the iris and a posterior chamber 24 behind the iris. The lens 16 is connected by zonular fibers 26 to a peripheral muscle about the lens known as the ciliary sulcus 28.

When the natural crystaline lens 16, which in a normal healthy condition is transparent, becomes cloudy and opaque to the transmission of light, a cataract condition exists and in order to correct this impairment, the cataract lens must be removed. The patient is then fitted with specially designed eyeglasses or with an intraocular lens to restore the patient's vision.

A variety of techniques exists for cataract lens removal but all entail forming an arcuate incision at the junction of the cornea 12 and the sclera 14. In some extracapsular techniques, an arcuate incision of 100 to 140 degrees may be required to remove a cataract lens.

Figure 2:
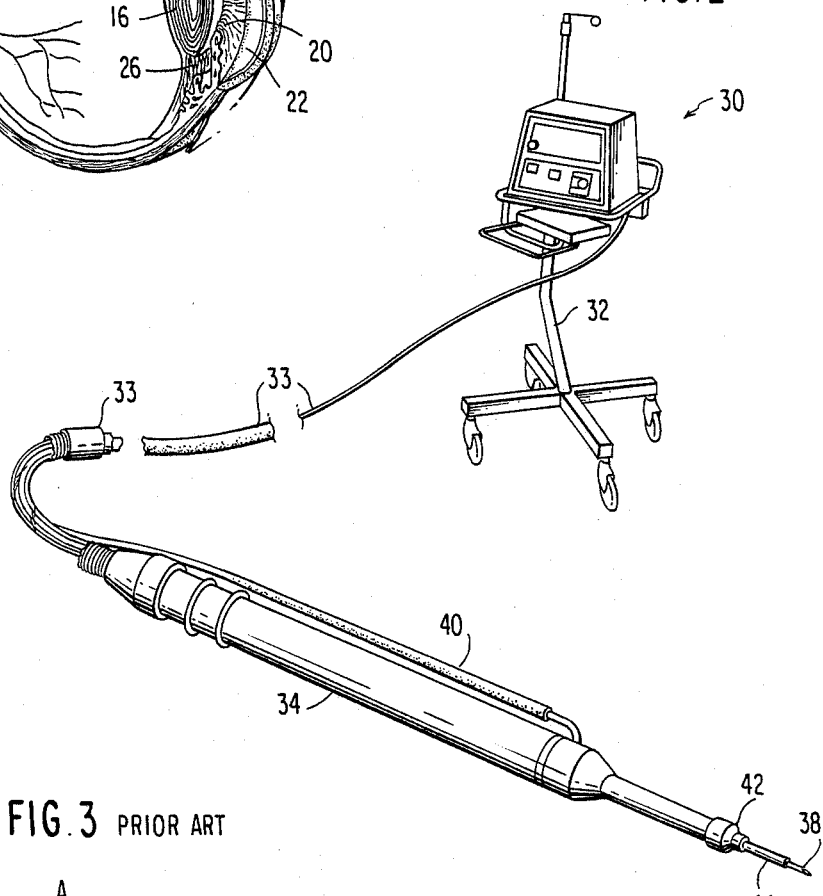
FIG. 2 is an axonometric view of a phacoemulsification and aspiration apparatus including a handpiece operable to emulsify and aspirate a cataract.
Figure 3:
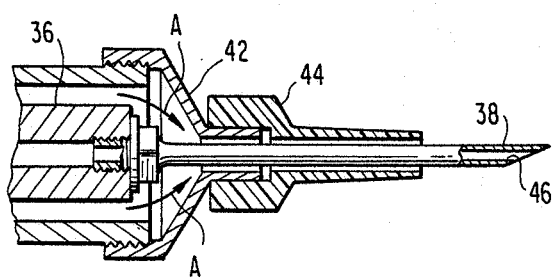
FIG. 3 is a cross-sectional detailed view of a tip portion of a Kelman prior art phacoemulsification and aspiration sleeve.

In the more recent past, however, a phacoemulsification and aspiration intracapsular technique has achieved a wide degree of success. One embodiment of a phacoemulsification apparatus and technique is disclosed in a Banko and Kelman U.S. Pat. No. 3,589,363. The disclosure of this Banko et al. patent is hereby incorporated by reference as though set forth at length. Briefly, however, as depicted in FIG. 2, a phacoemulsification and aspiration apparatus includes a fluid supply and ultrasonic power unit 30, which may be operably supported upon a portable stand 32, includes an ultrasonic oscillator source, a coolant and irrigating fluid supply and a vacuum pump. An umbilical cord 33 extends from the ultrasonic drive and fluid supply unit 30 to a handpiece 34. Internally, the handpiece includes an impedence transformer 36, note FIG. 3, which is electrically excited and can be made to vibrate with an ultrasonic frequency in the range of 25,000 to 100,000 cycles per second and higher. An emulsification tip 38 is axially aligned with and joined to a distal end of the impedance transformer. Accordingly, as the impedance tranformer vibrates longitudinally, the operating frequency will be transmitted directly into the tip or probe 38 to induce an axial vibratory motion at a high frequency.

A biologically inert cooling and irrigating fluid such as saline solution, is supplied under pressure to the handpiece 34 via line 40. An end cap 42 is fitted onto the handpiece and a sleeve 44 is in turn fitted onto the end cap. The sleeve 44 projects from the end cap coaxially with the vibratory tip 38 and is normally spaced therefrom so as to create an annular passage around the tip. Accordingly, saline cooling and lens irrigating solution passes in the direction of arrows "A" in FIG. 3 and coaxially bathes the vibratory tip 38 as it exits from the sleeve to irrigate lens material during aspiration.

The vibratory tip 38 is hollow and an axial bore 46 extends through the tip and is connected to a vacuum pump within the power unit 30 via the umbilical cord.

In operation, an incision is made in the corneal rim of 3 millimeters or so and the phacoemulsification tip 38 and surrounding sleeve 44 are inserted through the incision. The phacoemulsification tip 38, vibrating at an ultrasonic frequency, is manipulated into contact with a cataract lens and the high frequency vibrating tip serves to emulsify the lens within the lens capsular bag. The saline solution exiting from the elastomeric sleeve serves to suspend fine particulate matter of the emulsified lens and the suspension is aspirated through the axial bore 46.

Phacoemulsification/Irrigation and Aspiration Sleeve

Turning now specifically to FIGS. 4–7, there will be seen detailed views of a phacoemulsification/irrigation and aspiration sleeve 50 in accordance with one preferred embodiment of the invention. In this connection, the sleeve is formed with a hollow cylindrical base member 52 which is operable to be connected to a phacoemulsification/irrigation handpiece and coaxially extend about an elongate tip or probe 38. The hollow cylindrical base member 52 may be internally threaded and operably received upon a corresponding external thread of a handpiece end cap 42. An external portion of the base 52 may be fashioned with torque flats 54 or may be composed of a smooth cylindrical surface which may be frictionally engaged as desired.

Figure 4:
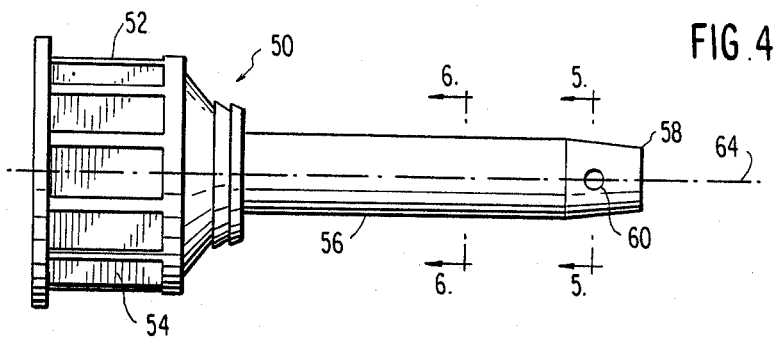
FIG. 4 is a side-elevational view of an improved phacoemulsification/irrigation and aspiration sleeve in accordance with one embodiment of the invention.
Figure 5:
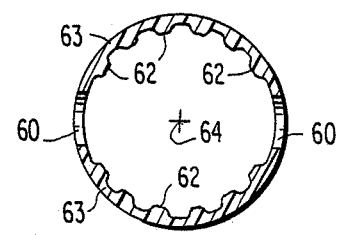
FIG. 5 is a cross-sectional view of a distal end of the sleeve taken along section line 5—5 in FIG. 4.

A cylindrical sleeve member 56 coaxially projects from the base 52 and is operable to surround an ultrasonic vibratory tip such as element 38 of a phacoemulsification and aspiration handpiece. As illustrated in FIGS. 4 and 5, a distal end 58 of the cylindrical sleeve member 56 includes one or more radial apertures 60 which are operably designed to facilitate fluid dispersion and the flow of saline solution through the sleeve and into the capsular bag of a patient's eye.

Figure 6:
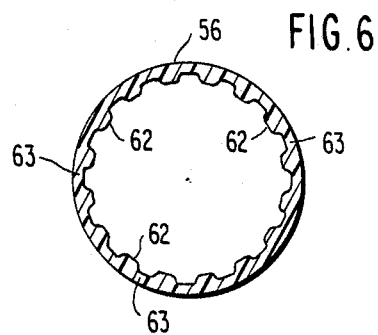
FIG. 6 is a cross-sectional view of the sleeve taken along section line 6—6 in FIG. 4.
Figure 7:
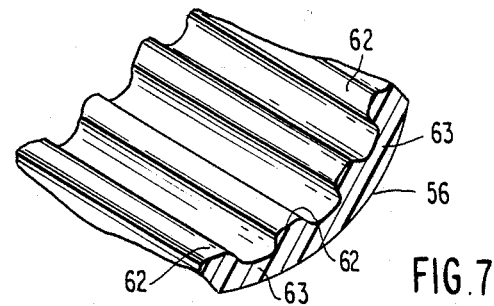
FIG. 7 is a detail fragment of a portion of the phacoemulsification/irrigation and aspiration sleeve in accordance with the invention disclosing a plurality of longitudinally extending internal ribs.

As shown in FIGS. 5, 6 and 7, it will be seen that the cylindrical sleeve member 56 is internally fashioned with a plurality of ridges 62 which radially project inwardly from the sleeve body 63. The raised ridges along the sleeve 56 extend longitudinally, in a preferred embodiment, and are mutually parallel and parallel with a central longitudinal axis 64 of the sleeve.

The longitudinally extending rib elements 62 of the sleeve 56 operably serve to guide cooling fluid along the exterior surface of an ultrasonic vibrating tip 38 to uniformally distribute cooling solution axially along the periphery of the vibrating tip. In addition, the longitudinal ribs 62 function to physically maintain separation between the sleeve body 63 and the ultrasonic vibrating tip 38. In this connection, it is often desirable to fabricate the sleeve from a rather flexible elastomeric composition to minimize any tendency of the sleeve to dampen vibratory motion of the probe. When a flexible sleeve is utilized, however, the sleeve may deflect, deform or collapse, as the sleeve bears against an incision in the eye, into frictional contact with the ultrasonic tip 38. With the instant invention, even though the crests of the ridges 62 may engage the vibrating tip during angular maneuvering procedures, the ridges 62 of the elastomeric sleeve will contact the axially vibrating tip while the next adjacent valley or body portion 63 of the sleeve will be free from contact with the tip. Accordingly, cooling solution will be permitted to axially flow about the periphery of the ultrasonic emulsification tip during all phases of a conventional phacoemulsification/irrigation and aspiration procedure.

In certain instances, the durometer rating of the sleeve polymer may be increased or the sleeve 56 may even by fabricated of a metallic material for irrigation and aspiration where vibratory tip damping is not considered critical.

Figure 8:
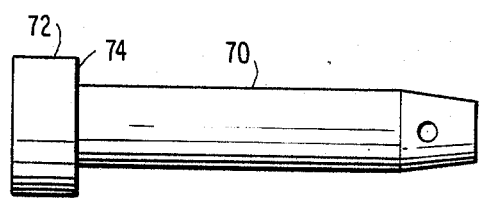
FIG. 8 is a side elevational view of an alternate preferred embodiment of the invention.

Turning to FIG. 8, there will be seen an alternate preferred embodiment of the invention. In this connection, a cylindrical sleeve member 70 is identical both externally and internally with sleeve member 56 in the first embodiment of the invention. A base portion 72 of the second embodiment, however, is externally provided with a peripheral lip 74 which is operable to receive a coaxial exterior retaining ring (not shown) which may be operably slid along the exterior surface of the cylindrical sleeve member 70. The retaining ring has an internal land area operable to engage the exterior peripheral lip 74 of the base and thereby serve to retain the base in a secure posture on a handpiece end cap.

Summary of Major Advantages of the Invention

After reading and understanding the foregoing description of the subject invention, in conjunction with the accompanying drawings, it will be appreciated that several distinct advantages of the phacoemulsification/irrigation and aspiration sleeve apparatus are obtained. Without attempting to set forth all of the desirable features of the embodiments of the subject invention, as specifically and inherently disclosed above, at least one of the illustrative advantages comprises the unique combination of a cylindrical sleeve for a phacoemulsification/irrigation and aspiration ultrasonic tip with at least one internal ridge to enhance the flow of fluid around a tip or probe. An elastomeric material may be used for the sleeve which will not dampen the vibratory action of the tip but at the same time will be effectively isolated from frictional contact with the tip during all phases of an operative phacoemulsification procedure. In this connection, although the longitudinally extending ribs 62 may contact the axially vibrating tip, the next adjacent valleys will be spaced from the tip. The space within the valley will permit cooling fluid to continue to flow about the ultrasonic tip in a peripheral manner thus eliminating any tendency for the generation of excessive heat during the phacoemulsification procedure.

The longitudinally extending parallel ribs 62 further function to channel the flow of irrigating fluid in a laminer manner along the axially vibrating tip to enhance cooling of the tip. Still further, the longitudinally extending ribs 62 enhance the structural integrity of the elongate sleeve portion 56 to facilitate maintaining a uniform annular zone about the ultrasonic tip.

In one preferred embodiment, a base member is internally threaded and therefore may be directly turned onto an end cap of a hand piece for a unitary replacement procedure. In another embodiment, the base member is provided with an external peripheral rim operable to be engaged by an internal peripheral land of a retaining collar which may then be screwed onto an end cap of a handpiece.

In addition to being utilized with a phacoemulsification and aspiration handpiece, it has been found that the subject invention is also useful with an irrigation and aspiration system to facilitate a uniform flow of irrigating fluid around an aspirating probe.

In describing the invention, reference has been made to preferred embodiments and illustrative advantages of the invention. Those skilled in the art, however, and familiar with the disclosure of the subject invention may recognize additions, deletions, modifications, substitutions, and/or other changes which will fall within the purview of the subject invention and claims.

I claim:

1. A phacoemulsification/irrigation and aspiration sleeve apparatus for a phacoemulsification/irrigation and aspiration device which includes a handpiece enhousing an ultrasonic vibratory drive assembly and a cylindrical ultrasonic tip member connected to the drive assembly for contacting and emulsifying a cataract lens, said sleeve apparatus comprising:
- a hollow cylindrical base member operable to be connected to the handpiece and to coaxially surround the elongate cylindrical tip;
- a cylindrical sleeve member connected to said base and coaxially projecting from the base along the elongate cylindrical top toward a distal end thereof, said cylindrical sleeve member being composed of a material having a pliable elastomeric composition;
- said cylindrical sleeve member having an internal diameter greater than the external diameter of the cylindrical ultrasonic tip member and thereby forming an annular passage around the ultrasonic tip, said cylindrical sleeve being operable to conduct a tip cooling and lens irrigating fluid around the ultrasonic tip and into a zone of lens emulsification at the distal end of the ultrasonic tip member; and
- said cylindrical sleeve member having a plurality of rib members for guiding cooling and irrigating fluid through said cylindrical sleeve member and for isolating interior wall portions of said cylindrical sleeve member from the exterior surface of the ultrasonic tip member.

2. A phacoemulsification/irrigation and aspiration sleeve apparatus as defined in claims 1 wherein:
- said plurality of ribs extend in a mutually parallel longitudinal posture and parallel with a central longitudinal axis of said cylindrical sleeve and the ultrasonic tip member.

3. A phacoemulsification/irrigation and aspiration sleeve apparatus as defined in claim 2 wherein:
- said hollow cylindrical base member is internally threaded to facilely screw said sleeve apparatus coaxially onto a compatibly threaded portion of the handpiece.

4. An irrigation and aspiration sleeve apparatus for an irrigation and aspiration device which includes a handpiece enhousing an elongate cylindrical tip member for irrigating and aspirating lens materials from an eye, said sleeve apparatus comprising:
- a hollow cylindrical base member operable to be connected to the handpiece and to coaxially surround the elongate cylindrical tip;
- a cylindrical sleeve member connected to said base and coaxially projecting from the base along the elongate cylindrical tip toward a distal and thereof, said cylindrical sleeve member being composed of a pliable elastomeric material;
- said cylindrical sleeve member having an internal diameter greater than the external diameter of the cylindrical tip member and thereby forming an annular passage around the ultrasonic tip, said cylindrical sleeve being operable to conduct a lens irrigating fluid around the tip and into a zone of lens irrigation and aspiration at the distal end of the tip member; and
- said cylindrical sleeve member having a plurality of internal, rib members for guiding irrigating fluid through said cylindrical sleeve member and to isolate interior wall portions of said cylindrical sleeve member from the exterior surface of the tip member.

5. An irrigation and aspiration sleeve apparatus as defined in claims 7 wherein:
- said plurality of ribs extend in a mutually parallel longitudinal posture and parallel with a central longitudinal axis of said cylindrical sleeve and the tip member.

* * * * *